United States Patent [19]

Berger et al.

[11] 4,331,519

[45] May 25, 1982

[54] PROCESS FOR THE PRODUCTION OF ((MONO-TRICHLORO)-TETRA-(MONOPOTASSIUM-DICHLORO))-PENTA-ISOCYANURATE)

[75] Inventors: Michael Berger, Hemmerich; Edgar Koberstein, Alzenau, both of Fed. Rep. of Germany

[73] Assignee: Degussa Aktiengesellschaft, Frankfurt, Fed. Rep. of Germany

[21] Appl. No.: 222,672

[22] Filed: Jan. 5, 1981

[30] Foreign Application Priority Data

Jan. 7, 1980 [DE] Fed. Rep. of Germany ....... 3000365

[51] Int. Cl.$^3$ ............................ C25B 3/10; C25B 3/02
[52] U.S. Cl. ......................................... 204/72; 204/78; 544/190
[58] Field of Search .................... 204/59 R, 72, 73 R, 204/74, 78

[56] References Cited

U.S. PATENT DOCUMENTS

| 3,150,132 | 9/1964 | Symes | 544/190 |
| 3,616,445 | 6/1971 | Bianchi | 204/290 F |
| 4,118,569 | 10/1978 | Berkowitz | 544/190 |
| 4,127,454 | 11/1978 | Torii et al. | 204/59 R |
| 4,127,455 | 11/1978 | Schulz et al. | 204/78 |

FOREIGN PATENT DOCUMENTS 1814567 8/1969 Fed. Rep. of Germany.
1671422 10/1971 Fed. Rep. of Germany.

OTHER PUBLICATIONS

Alenaar et al, Chem. Abs., vol. 83, abstract 97389h (1975).

Primary Examiner—F. Edmundson
Attorney, Agent, or Firm—Cushman, Darby & Cushman

[57] ABSTRACT ((Mono-trichloro)-tetra-(monopotassium-dichloro))-penta-isocyanurate is produced from cyanuric chloride in an electrolytic process by reacting it at the anode in an aqueous medium containing potassium ions under the influence of a direct current voltage.

17 Claims, No Drawings

PROCESS FOR THE PRODUCTION OF ((MONO-TRICHLORO)-TETRA-(MONOPOTASSIUM-DICHLORO))-PENTA-ISOCYANURATE)

BACKGROUND OF THE INVENTION

It is known to produce ((mono-trichloro)-tetra-(monopotassium dichloro))-penta-isocyanurate by reacting either tripotassium cyanurate with chlorine or potassium dichloroisocyanurate with hydrogen chloride or trichloroisocyanuric acid in aqueous medium at a temperature of 0° to 50° C. (Symes U.S. Pat. No. 3,150,132). It is also known that ((mono-trichloro)-tetra(monopotassium-dichloro))-penta-isocyanurate is formed if potassium dichloroisocyanurate monohydrate and trichloroisocyanuric acid are brought together as solids under high pressure (Berkowitz U.S. Pat. No. 4,118,569). In each case, the starting material is cyanuric acid or at last cyanuric chloride. The materials provided for the reaction must first be produced in partly expensive manner from the cyanuric acid or the cyanuric chloride. The yields of ((mono-trichloro)-tetra-(monopotassium-dichloro-))-penta-isocyanurate based on the cyanuric acid or the cyanuric chloride as starting material are below 80% and therefore are unsatisfactory.

SUMMARY OF THE INVENTION

There has now been found a process for the production of ((mono-trichloro)-tetra-(monopotassium-dichloro))-penta-isocyanurate which is characterized by reacting cyanuric chloride in an aqueous, potassium ion containing medium at an anode. In this process, in a simple manner, the cyanuric chloride is converted directly into ((mono-trichloro)-tetra-((monopotassium-dichloro))-penta-isocyanurate and there is hereby a substantially better yield than is produced in the known process.

According to the invention the reaction of the cyanuric chloride takes place in aqueous medium. The concentration of the cyanuric chloride can be chosen as desired in a wide range. Generally, it is advantageous if per gram of cyanuric chloride there are present 2 to 50 ml, especially 5 to 20 ml of water. The pH value of the medium during the reaction suitably is held to 1 to 12, preferably to 3 to 7, especially to 3 to 6. Alkaline acting materials are added to adjust the pH. Preferably potassium hydroxide is used. In many cases, it can be advantageous to add additionally a potassium salt, preferably potassium chloride. The ratio of potassium ions to cyanuric chloride can be chosen in a wide range, both stoichiometric as well as under or over stoichiometric being usable. However, it is generally suitable that at least stoichiometric amounts of potassium ions be present. The molar ratio of potassium to cyanuric chloride preferably is 0.8 to 10:1, particularly 2 to 7:1.

Suitably the medium is held during the reaction to a temperature of 5° to 50° C., perferably from 5° to 30° C., especially from 10° to 25° C.

The reaction of the cyanuric chloride in the medium takes place according to the invention under the influence of a direct current voltage at the anode. With advantage the voltage between anode and cathode is regulated to 1 to 20, especially to 4 to 8 volts. The current density suitably amounts to 100 to 20,000, preferably 500 to 10,000, especially 1000 to 5000, amperes per $m^2$ of electrode surface.

All the customary electrodes can be used for the reaction, which are suited for maintaining the reaction conditions and consist of materials which are at least substantially inert to the reacting materials and the materials formed in the reaction. Chiefly suited are electrodes which generally are employed for the production of chlorine and alkali by electrolysis. For example, there can be used graphite electrodes or metal electrodes of the platinum metals or in a given case, iron plated with a platinum metal, nickel, stainless steel or titanium and as anodes, preferably electrodes according to German OS No. 1671422 or German OS No. 1814567 (and related Bianchi U.S. Pat. No. 3,616,445), which consist of a metal nucleus and a metallic or metal oxide coating, especially titanium electrodes coated with ruthenium oxide. The entire disclosures of the two German OS and the Bianchi U.S. Patent are hereby incorporated by reference and relied upon.

In an especially preferred illustrative form the cathode space is separated from the anode space, for example by an ion exchange membrane. In this case, the cathode space is charged with a dilute solution of potassium hydroxide, which preferably contains 1 to 10, especially 2 to 4, percent by weight of potassium hydroxide, and the anode space is charged with the liquid providing the reaction medium which is substantially saturated with cyanuric chloride, has a pH of 3 to 7 and contains an over stoichiometric amount of potassium ions. With particular advantage this process is designed for continuous operation and for this purpose the liquid is led through the cathode space as well as through the anode space in a continuous flow.

Unless otherwise indicated all parts and percentages are by weight.

The process can comprise, consist essentially of or consist of the steps set forth with the stated materials.

DETAILED DESCRIPTION

Example 1

There was used a cell in which the anode space was separated from the cathode space by a cation exchange membrane. The cathode was made of stainless steel (V4A-steel) and had a surface area of 54 $cm^2$. The anode consisted of titanium which was coated with ruthenium oxide and had a surface area of 30 $cm^2$. At the beginning the cathode space was filled with 500 ml of a 3 percent aqueous potassium hydroxide and the anode space filled with a solution of 50 grams of cyanuric chloride and 75 grams of potassium chloride in 750 ml of water, the solution being adjusted to a pH of 4.5 by means of potassium hydroxide. It was operated at a voltage of 6 volts and a current strength of 8 amperes. The temperature was 15° C. During the reaction water was fed into the cathode space in a continuous flow and there was fed into the anode space a 6 percent aqueous cyanuric chloride solution adjusted to a pH of 4.5 by means of potassium hydroxide, as well as potassium hydroxide solution to such an extent that the pH was always maintained at 4.5 in the anode space. The potassium hydroxide solution formed in the cathode space was continuously drawn off therefrom. It was used for the adjustment of the pH in the cyanuric chloride solution or in the anode space. The ((mono-trichloro)-tetra-(monopotassium-dichloro))-penta-isocyanurate separated out in the anode space as a colorless, crystalline material. This was discharged with the liquid that was delivered from the anode space and separated from the liquid by filtration.

The liquid was brought to 6% content by addition of cyanuric chloride, regulated to a pH of 4.5 by means of potassium hydroxide and recycled into the the anode space. The ((mono-trichloro)-tetra-(monopotassium-dichloro))-penta-isocyanurate filtered off was washed with a little water and dried. It had a content of active chlorine of 67%. The yield amounted hourly to 14.1 grams, corresponding to 98%, based on the cyanuric chloride employed.

Example 2

The procedure was as in Example 1, but the temperature of the medium in the cell was held at 25° C., The hourly yield was 13.8 grams, corresponding to 95% based on the cyanuric chloride employed.

Example 3

The procedure was as in Example 1 but the process was operated at a current strength of 6 amperes. The hourly yield was 14.0 grams, corresponding to 97% based on the cyanuric acid employed.

Example 4

The procedure was as in Example 1 but there was used an anode made of platinum (surface area 30 cm$^2$) and the process was operated at a current strength of 10 amperes. The hourly yield was 13.5 grams, corresponding to 94% based on the cyanuric chloride employed.

The entire disclosure of German priority application No. P 3000365.7 is hereby incorporated by reference.

What is claimed is:

1. A process for the production of ((mono-trichloro)-tetra-(mono-potassium-dichloro))-penta-isocyanurate comprising carrying out the process electrolytically at an anode employing cyanuric chloride in an aqueous, potassium ion containing medium.

2. A process according to claim 1 wherein the reaction medium has a pH of 3 to 7.

3. A process according to claim 2 wherein the reaction is carried out at a temperature of 5° to 30° C.

4. A process according to claim 1 wherein the reaction is carried out at a temperature of 5° to 30° C.

5. A process according to claim 1 wherein the reaction is carried out at a voltage of 1 to 20 volts and a current density of 100 to 20,000 amperes per m$^2$ of electrode surface.

6. A process according to claim 5 wherein the voltage is 4 to 8 volts and the current density is 1000 to 5000 amperes per m$^2$ of electrode surface.

7. A process according to claim 4 wherein the voltages is 4 to 8 volts and the current density is 1000 to 5000 amperes per m$^2$ of electrode surface.

8. A process according to claim 3 wherein the voltage is 4 to 8 volts and the current density is 1000 to 5000 amperes per m$^2$ of electrode surface.

9. A process according to claim 2 wherein the voltage is 4 to 8 volts and the current density is 1000 to 5000 amperes per m$^2$ of electrode surface.

10. A process according to claim 1 wherein the voltage is 4 to 8 volts and the current density is 1000 to 5000 amperes per m$^2$ of electrode surface.

11. A process according to claim 10 wherein the reaction is carried out in an anode space separated from the cathode space.

12. A process according to claim 9 wherein the reaction is carried out in an anode space separated from the cathode space.

13. A process according to claim 8 wherein the reaction is carried out in an anode space separated from the cathode space.

14. A process according to claim 7 wherein the reaction is carried out in an anode space separated from the cathode space.

15. A process according to claim 6 wherein the reaction is carried out in an anode space separated from the cathode space.

16. A process according to claim 2 wherein the reaction is carried out in an anode space separated from the cathode space.

17. A process according to claim 1 wherein the reaction is carried out in an anode space separated from the cathode space.

* * * * *